United States Patent [19]

Walker

[11] 4,159,722
[45] Jul. 3, 1979

[54] PRESSURE REGULATOR FOR ENDOTRACHEAL TUBE CUFF OR THE LIKE

[75] Inventor: Clarence L. Walker, Webster Groves, Mo.

[73] Assignee: Sherwood Medical Industries, Inc., St. Louis, Mo.

[21] Appl. No.: 782,221

[22] Filed: Mar. 28, 1977

[51] Int. Cl.² .......................................... A61M 25/00
[52] U.S. Cl. .................................. 137/496; 128/351; 137/498; 137/557
[58] Field of Search ................ 128/351; 137/496, 498, 137/557

[56] References Cited

U.S. PATENT DOCUMENTS

| | | | |
|---|---|---|---|
| 2,710,626 | 6/1955 | Burdick et al. | 137/498 |
| 3,390,696 | 6/1968 | Dawson | 137/496 |
| 3,529,596 | 9/1970 | Gardner | 128/351 X |
| 3,731,691 | 5/1973 | Chen | 128/351 |
| 3,794,043 | 2/1974 | McGinnis | 128/351 X |

FOREIGN PATENT DOCUMENTS 530987  5/1976  U.S.S.R. ................................. 137/498

Primary Examiner—Robert G. Nilson
Attorney, Agent, or Firm—Paul L. Gardner

[57] ABSTRACT

An improved pressure regulator for an inflatable cuff on an endotracheal tube or the like includes a housing which contains a valve assembly and a pressure regulating chamber. The housing is adapted to be connected to an inflatable cuff so that the pressure regulating chamber communicates with the cuff through the valve assembly. The valve assembly (1) permits slow increases in air pressure in the cuff to be transferred into the pressure regulating chamber, thereby preventing over-inflation of the cuff, and (2) closes in response to relatively rapid pressure changes in the cuff to prevent collapsing of the cuff when the pressure of the air or other gas delivered through the endotracheal tube (e.g., by a respirator) is relatively high. A spring-biased piston is disposed in the pressure regulating chamber for regulating the pressure in an inflatable cuff to which the regulator housing is connected, and a rolling diaphragm covers the piston. The housing is constructed of a transparent material so as to provide attending personnel with a visual indication of the pressure in the pressure regulating chamber and a cuff to which the housing is connected.

14 Claims, 9 Drawing Figures

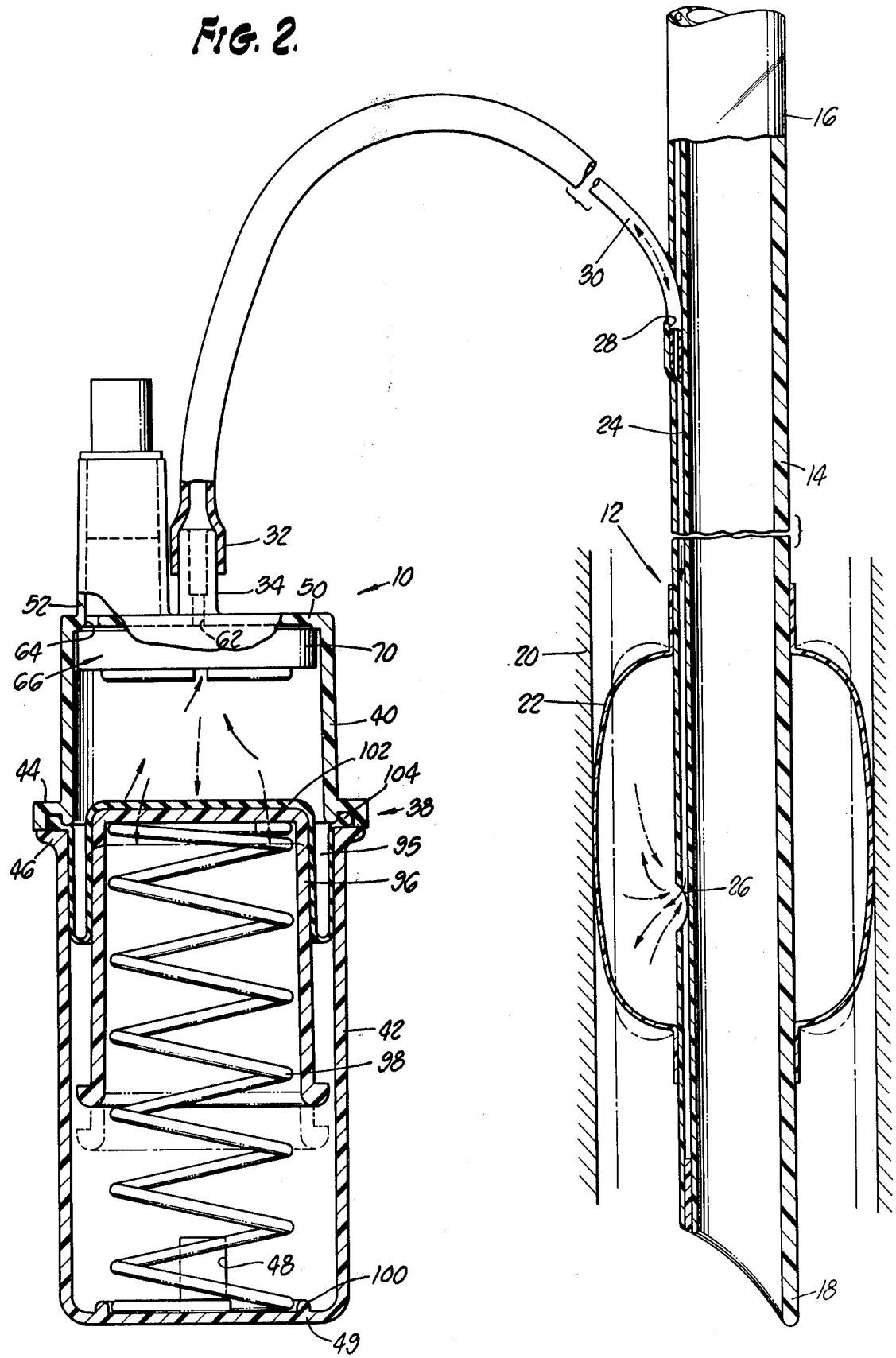

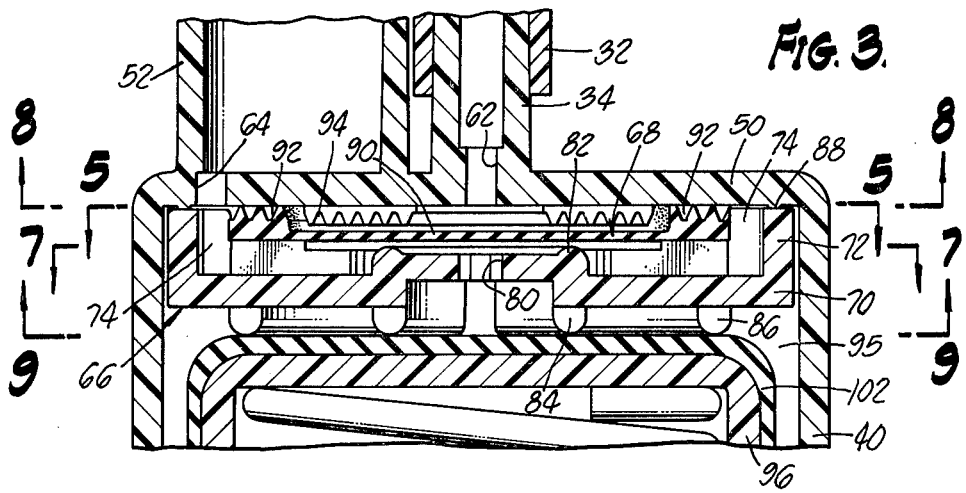
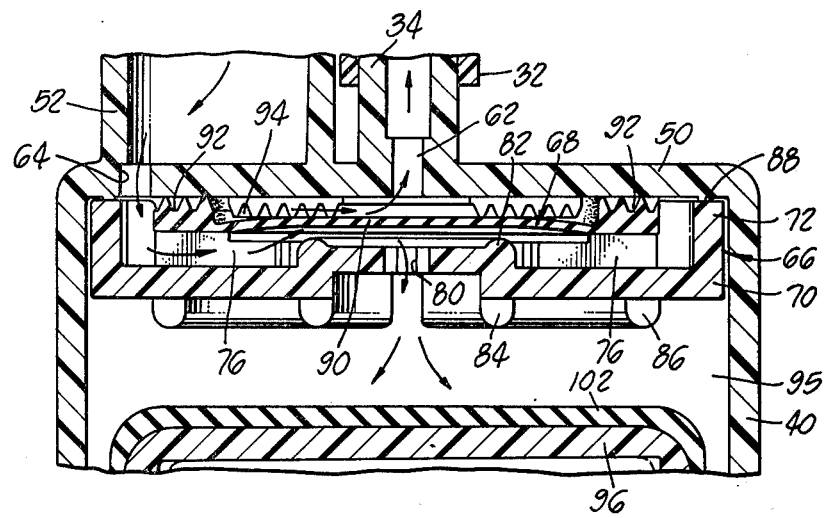
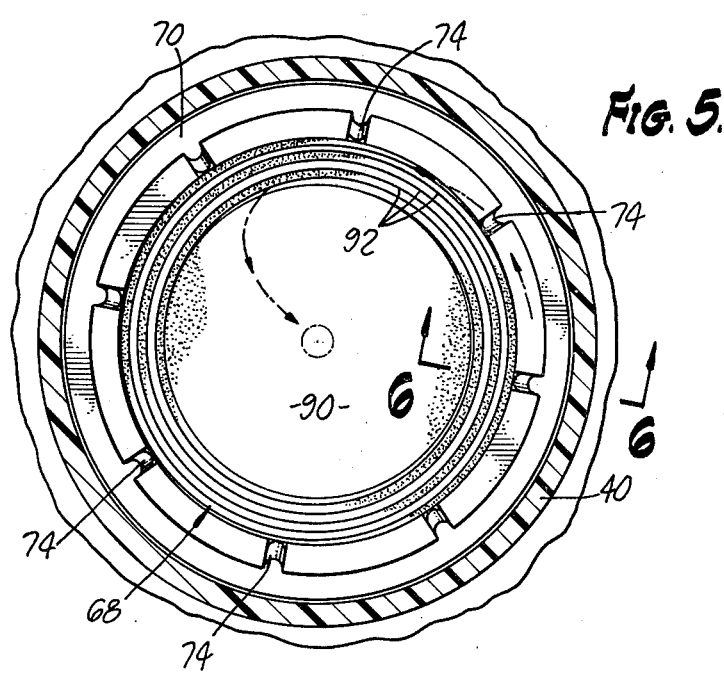
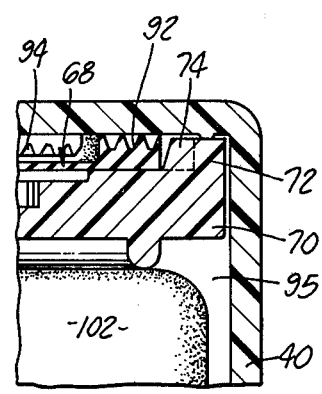

PRESSURE REGULATOR FOR ENDOTRACHEAL TUBE CUFF OR THE LIKE

FIELD OF THE INVENTION

The present invention relates to an improved pressure regulator for regulating the pressure of air in an inflatable member, such as an inflatable cuff on an endotracheal tube or the like.

BACKGROUND OF THE INVENTION

In the medical treatment of patients requiring breathing assistance it is common to insert an endotracheal tube into the trachea of the patient by way of the mouth or nose or by way of a surgically created opening into the patient's trachea. The rear or proximal end of the endotracheal tube is connected to a breathing apparatus, such as a respirator, which will periodically force air into the lungs through the tube. The inner or distal end of the tube is typically provided with an annular, inflatable cuff which is inflated after the tube is inserted into the patient's trachea to provide a seal against the interior wall of the trachea. The cuff is inflated by means of a conventional syringe which forces air into the cuff through a relatively small diameter secondary tube, known as a lumen or tubule, provided in the wall of the endotracheal tube.

By way of example, endotracheal tubes provided with inflatable, trachea-sealing cuffs on the inner or distal end thereof are shown in U.S. Pat. Nos. 3,402,718; 3,504,676; 3,565,079; 3,642,005; 3,693,624; 3,794,036; 3,794,043; 3,848,605; and 3,901,246.

One of the problems associated with the use of an endotracheal tube having an inflatable, trachea-sealing cuff on its distal end is that there is a tendency to over-inflate the cuff so that it may press too tightly against the tracheal wall. Over-inflation causes discomfort to the patient and also can cause such serious complications as dilation of the trachea, blockage of blood circulation and necrosis of that portion of the trachea around the cuff.

Various ways have been proposed to prevent over-pressurizing of such cuffs. For example, U.S. Pat. No. 3,642,005 discloses an endotracheal tube with an inflatable cuff and a pressure-regulating balloon connected to the cuff. The balloon is of such a character that it will expand to a size at which the air pressure in it is the same as the maximum air pressure desired in the cuff, after which the balloon will expand further without increasing that maximum pressure as additional air is forced into the cuff. However, the pressure-regulating balloon of the U.S. Pat. No. 3,642,005 gives rise to another problem. The breathing apparatus (e.g., a respirator) connected to the endotracheal tube sometimes intermittently delivers air through the endotracheal tube and to the patient at such high pressures that it compresses the cuff and forces air back into the balloon, thereby breaking the seal between the cuff and the trachea wall so that air delivered by the breathing apparatus can escape between the cuff and the interior wall of the trachea. In an effort to overcome this problem, U.S. Pat. No. 3,794,043 proposes the use of a check valve between the pressure-regulating balloon and the inflatable cuff. The check valve of the U.S. Pat. No. 3,794,043 closes when there is an increase in air pressure at the distal end of the cuff (such as may occur every time the breathing apparatus forces a charge of air or other gas into the lungs) to prevent air from the cuff from being forced back into the balloon. However, the device of the U.S. Pat. No. 3,794,043 gives rise to another problem. Air (or other gas) from the breathing apparatus which is connected to the endotracheal tube can migrate through the material of the inflatable cuff and thereby over-pressurize the cuff. It is desirable to relieve this over-pressurization of the inflatable cuff. However, since the check valve of the U.S. Pat. No. 3,794,043 closes when the pressure in the inflatable cuff exceeds the pressure in the regulating balloon, the cuff remains overpressurized.

OBJECTS AND SUMMARY OF THE INVENTION

It is an object of the present invention to provide an improved pressure regulator for an inflatable member.

A more specific object of the present invention is to provide an improved pressure regulator for an inflatable cuff on an endotracheal tube or the like which overcomes the aforementioned disadvantages associated with prior art pressure regulators.

Another object of the present invention is to provide an improved pressure regulator for an inflatable cuff on an endotracheal tube or the like having an improved valve assembly which (1) prevents relatively rapid pressure increases imposed by a breathing apparatus to which the endotracheal tube is connected from collapsing the inflatable cuff to prevent the escape of air between the cuff and the wall of the trachea, and (2) permits relatively slow pressure increases in the inflatable cuff to be transferred into the regulator, thereby preventing over-inflation of the cuff.

It is a further object of the present invention to provide an improved pressure regulator for inflatable cuffs on endotracheal tubes and the like which provides attending personnel with a visual indication of the air pressure in the system (i.e., the inflatable cuff and the pressure regulator).

The foregoing and other objects and advantages have been realized by the improved pressure regulator of the present invention, which comprises a housing adapted to be connected to an inflatable cuff on an endotracheal tube or the like. A pressure regulating chamber and a valve assembly are disposed in the housing and a spring-biased piston is disposed in the pressure regulating chamber. The valve assembly includes a valve member provided with a flow restricting passage which permits relatively slow increases in pressure in the inflatable cuff to be transferred to the pressure regulating chamber. The valve assembly closes in response to rapid or sudden pressure increases in the inflatable cuff (such as may be created, for example, by intermittent peak pressures of air delivered to the patient by a breathing apparatus attached to the endotracheal tube) to prevent the transference of such sudden pressure increases to the pressure regulating chamber. The pressure regulator housing is transparent so that attending personnel may visualize the position of the piston in the pressure regulating chamber to determine the pressure in the system.

BRIEF DESCRIPTION OF THE DRAWINGS

In the drawings:

FIG. 2 is a sectional elevation view of the pressure regulator of the present invention, similar to FIG. 1, but showing the various parts in the position they occupy after the cuff has been inflated.

FIG. 3 is a partial sectional elevation view showing the valve assembly of the pressure regulator of the present invention prior to the time that air is introduced through the valve assembly to inflate the cuff to which the regulator is connected.

FIG. 4 is a sectional elevation view of the valve assembly of the pressure regulator of the present invention showing the parts in the position they occupy while the inflatable cuff to which the pressure regulator is connected is being inflated.

FIG. 5 is a cross-section taken along the plane 5—5 of FIG. 3 and showing the top portions of the flexible diaphragm valve of the valve assembly of the pressure regulator of the present invention and the valve housing which retains the diaphragm valve.

FIG. 6 is a partial sectional elevation view taken along the plane 6—6 of FIG. 5 showing the outer peripheral portion of the flexible diaphragm valve and the valve housing which retains the diaphragm valve in the valve assembly of the pressure regulator of the present invention.

DETAILED DESCRIPTION OF PREFERRED EMBODIMENT

Figure 1:
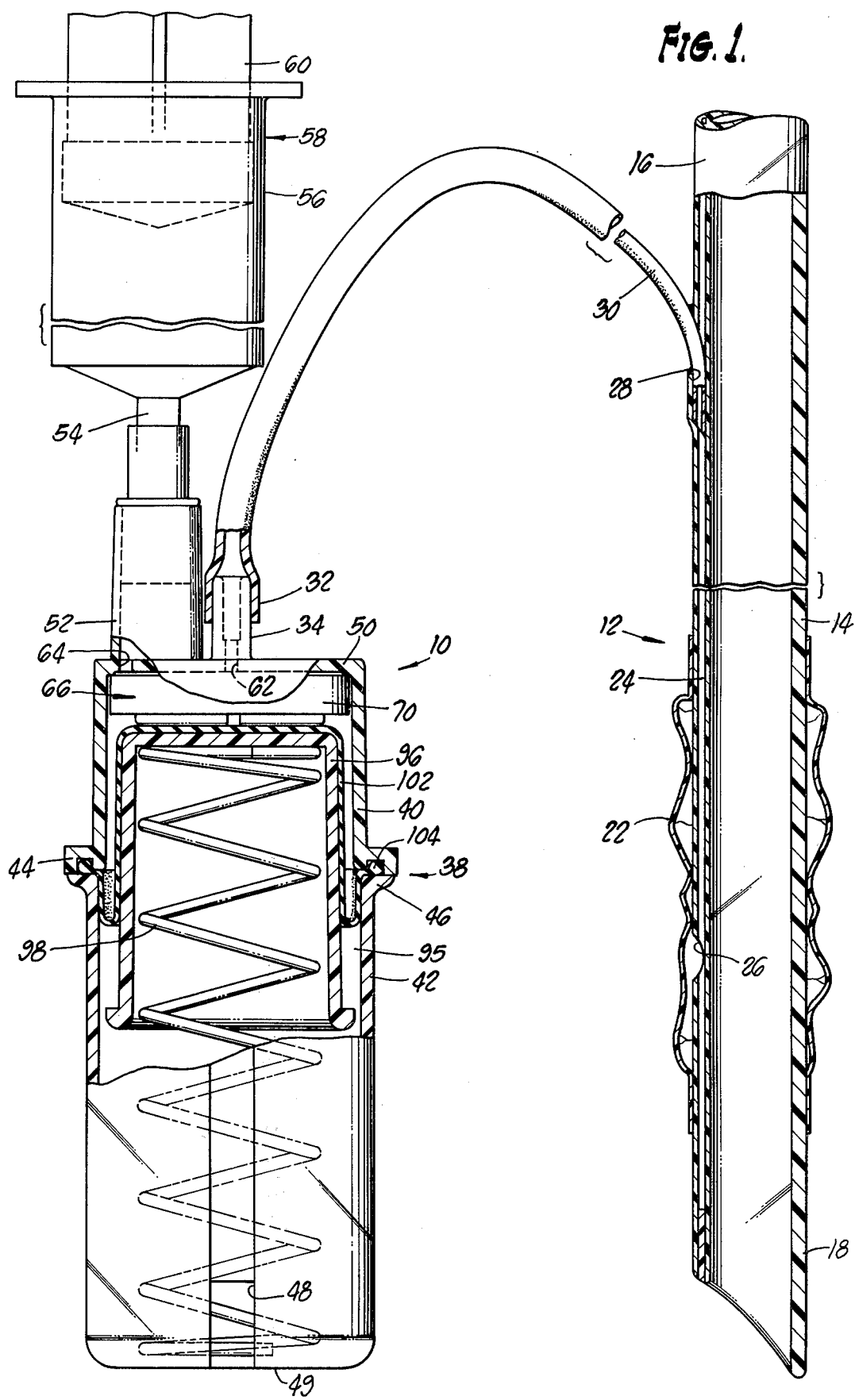
FIG. 1 is a sectional elevation view showing a preferred embodiment of the improved pressure regulator of the present invention connected to an inflatable cuff on an endotracheal tube, with the parts illustrated as they appear prior to the time that the cuff is inflated.

As shown in FIGS. 1 and 2, the improved pressure regulator 10 of the present invention is adapted to be connected to and used in conjunction with an endotracheal tube assembly 12.

The endotracheal tube assembly 12, which is conventional per se, includes an elongated, generally flexible tube 14 having an outer or proximal end 16 which is adapted to be connected to a breathing apparatus (e.g., a respirator) or the like, not shown, and an inner or distal end 18 which is adapted to be inserted into the trachea (schematically illustrated at 20 in FIG. 2) of a patient to whom breathing assistance is to be administered. An inflatable cuff 22 (e.g., of a soft plastic material) encircles the endotracheal tube 14 adjacent the distal end 18 thereof. The inflatable cuff 22 is in fluid communication with a relatively small diameter passage 24 (generally known in the art as a lumen) which is formed in the wall of the endotracheal tube 14. An opening 26 in the lumen 24 establishes fluid communication between the lumen and the interior of the inflatable cuff 22, and another opening 28 spaced from the inflatable cuff 22 is provided in the lumen 24 for accommodating one end of a connecting tube 30. The tube 30 has its outer end 32 connected to a fitting 34 on the pressure regulator 10 of the present invention for permitting inflation of the inflatable cuff 22 and regulation of the pressure within the cuff, in a manner described hereinafter.

As shown in FIG. 2, when the cuff 22 is inflated it engages the interior wall of the patient's trachea 20 to prevent air delivered through the endotracheal tube 14 from escaping between the exterior of the tube 14 and the interior wall of the trachea 20.

The pressure regulator 10 of the present invention includes a housing 38 (preferably of a generally cylindrical configuration) having a forward section 40 and a rear section 42. The rear end of the forward section 40 is provided with an annular flange 44 thereon and the rear section 42 is provided with an annular flange 46 on the forward end thereof. The forward and rear sections 40 and 42 of the housing 38 are preferably constructed of a relatively clear plastic material for permitting visual inspection of the interior of the housing, and the annular flanges 44 and 46 are welded or otherwise suitably secured to one another. The rear end of the rear section 42 of the housing 38 is provided with an opening 48 adjacent the rear end wall 49 thereof so that the rear end of the housing 38 communicates with the atmosphere. (See FIGS. 1 and 2.)

The forward section 40 of the housing 38 has a forward end wall 50 upon which fittings 34 and 52 are integrally formed. As mentioned above, fitting 34 is adapted to receive one end 32 of a connecting tube 30 which leads to the lumen 24 in the endotracheal tube assembly 12 for establishing fluid communication between the pressure regulator 10 and the inflatable cuff 22 on the endotracheal tube 14. The other fitting 52 on the forward end wall 50 of the pressure regulator 10 is adapted to receive the outlet end 54 of the barrel 56 of a conventional syringe 58. The syringe 58, which includes the barrel 56 and a plunger 60, is provided for selectively inflating the cuff 22 on the endotracheal tube 14 in a manner described hereinafter.

A check valve (not shown) is provided in the fitting 52 which receives the outlet end or tip 54 of the barrel 56 of the syringe 58. The check valve (not shown) is automatically opened by the syringe tip 54 when the tip 54 is inserted into the fitting 52. Air can be introduced into the pressure regulator 10 and the inflatable cuff 22 of the endotracheal tube assembly 12, in a manner described hereinafter, when the syringe tip 54 is inserted into the fitting 52 and the plunger 60 of the syringe is pushed forwardly (i.e., downwardly, as viewed in FIG. 1) in the barrel 56.

The forward end wall 50 of the forward housing section 40 of the pressure regulator 10 is provided with a central opening 62 in alignment with the central fitting 34 so that the interior of the housing 38 communicates with the connecting tube 30 and the lumen 24 on the endotracheal tube 14. Another opening 64 is provided adjacent the outer periphery edge of the forward end wall 50 of the forward housing section 40 so that the interior of the housing 38 of the pressure regulator 10 can communicate with the barrel 56 of the syringe 58 through the syringe fitting 52 (FIG. 1) and the check valve (not shown) therein.

Disposed within the housing 38 adjacent the forward end wall 50 thereof is a valve assembly 66. As best shown in FIGS. 3 and 4, the valve assembly includes a flexible (e.g., silicone rubber) valve disc 68 which resides in a valve chamber in the generally cup-shaped valve housing 70.

Figure 7:
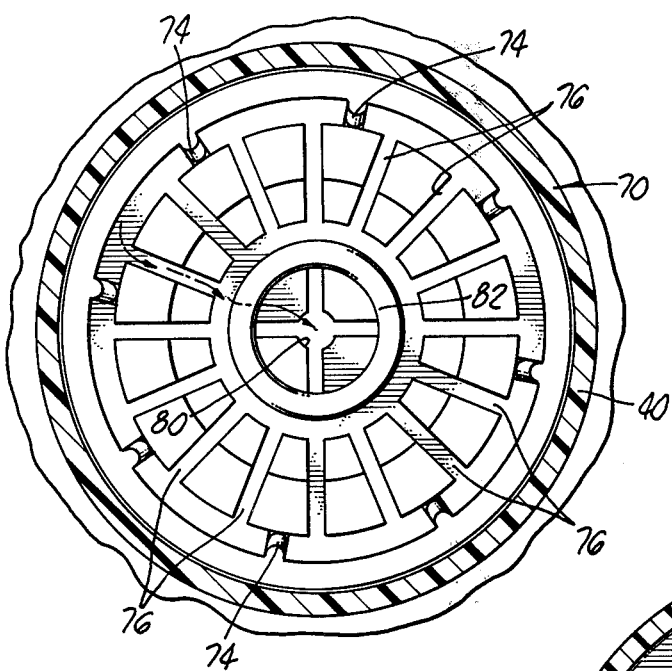
FIG. 7 is a sectional plan view taken along the plane 7—7 of FIG. 3 and showing the top surface of the valve housing which houses the flexible diaphragm valve in the valve assembly of the pressure regulator of the present invention.

As best shown in FIGS. 3-7, the valve housing 70 includes an upstanding peripheral wall 72 having a plurality of circumferentially-spaced centering abutments 74, 74 . . . 74 (FIGS. 5-7) formed on the interior peripheral surface thereof for centering the flexible valve disc 68 in the housing. As best shown in FIG. 7, the forwardly facing surface of the housing 70 which supports the valve disc 68 is provided with a plurality of radially-extending, circumferentially-spaced slots 76, 76 . . . 76 which form air passages. An opening 80 extends through the central portion of the housing 70 and an upstanding annular valve seat 82 is formed around the opening 80.

Figure 9:
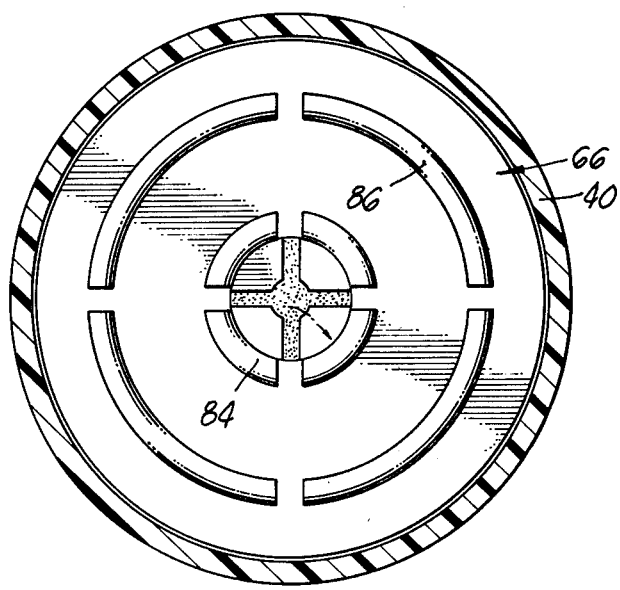
FIG. 9 is a sectional bottom plan view taken along the plane 9—9 of FIG. 3 and showing the bottom surface of the valve housing in the pressure regulator of the present invention.

Referring to FIG. 9, it will be seen that the rearwardly facing surface of the valve housing 70 is provided with a slotted, inner annular ridge 84 and a slotted outer annular ridge 86.

The upper annular surface of the upstanding peripheral wall 72 of the valve housing 70 is sealingly secured (e.g., welded) to the rearwardly facing surface of the forward end wall 50, as illustrated at 88 in FIGS. 3 and 4, to define a valve chamber in which the flexible valve disc 68 is disposed. The pressure regulator housing 38 and the valve housing 70 are both preferably made of a plastic material, and any suitable means may be employed to sealingly weld the valve housing 70 to the rearwardly facing surface of the forward end wall 50 of the regulator housing 38.

The flexible valve disc 68 includes a relatively thin central portion 90 which overlies the opening 80 in the valve housing 70, and a somewhat thicker outer peripheral portion provided with a spiral groove 92 which forms a flow-restricting air passage (see FIGS. 3-5) in the forwardly facing surface of the disc. The disc is shaped such that its central portion 90 is normally disposed away from the annular valve seat 82 so that the valve is normally open.

Figure 8:
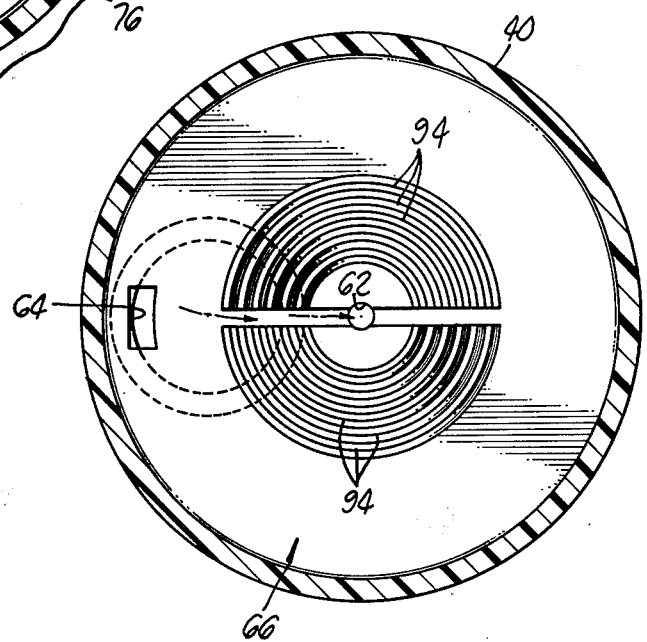
FIG. 8 is a sectional bottom plan view taken along the plane 8—8 of FIG. 3 and showing the bottom surface of the upper end wall of the housing of the pressure regulator of the present invention.

As best shown in FIGS. 3, 4 and 8, the rearwardly facing surface of the forward end wall 50 of the regulator housing 38 is provided with a plurality of radially-spaced ridges 94, 94 . . . 94 near the central portion thereof for preventing the central portion 90 of the valve disc 68 from sticking to the forward end wall 50.

The interior of the regulator housing 38 defines a piston chamber 95 between the rear end wall 49 and the valve assembly 66.

Referring to FIGS. 1 and 2, a piston member 96 is disposed in the piston chamber 95 in the regulator housing 38. The piston member 96 is a generally inverted cup-shaped member which is spring-biased toward the valve assembly 66 by means of a compression spring 98. The forward end of the compression spring 98 fits within the inverted cup-shape of the piston, and the rear end of the compression spring is retained by an upstanding annular boss 100 provided on the forwardly facing surface of the rear end wall 49 of the regulator housing 38 (see FIG. 2).

A rolling diaphragm 102 is disposed in the pressure regulator housing 38 and covers the piston member 96. The rolling diaphragm has its outer periphery 104 clamped and sealed between the peripheral flanges 44 and 46 on the forward and rear housing sections 40 and 42, respectively. The diaphragm 102 is referred to as a rolling diaphragm because it rolls along the outer peripheral wall of the piston 96 and the inner peripheral wall of the housing 38 as the piston moves in the housing (e.g., between the positions of the piston shown in FIGS. 1 and 2).

OPERATION

The preferred embodiment of the improved pressure regulator 10 of the present invention described above is adapted to be used in the following manner.

An endotracheal tube 14 to which the improved pressure regulator 10 of the present invention is adapted to be connected is inserted into the trachea of the patient to whom breathing assistance is to be administered. During insertion, the endotracheal tube 14 is in the condition shown in FIG. 1, with the inflatable cuff 22 in its deflated condition.

After the endotracheal tube 14 has been inserted to the desired depth in the trachea of the patient, the connecting tube 30 is connected to the outlet opening 28 of the lumen 24 in the wall of the endotracheal tube 14, and the other end 32 of the connecting tube 30 is attached to the fitting 34 on the central portion of the forward end wall 50 of the pressure regulator housing 38. Thereafter, the outlet end or tip 54 of the syringe 58 (FIG. 1) is inserted in the syringe fitting 52 on the pressure regulator housing 38 to open the check valve (not shown) in the fitting. The plunger 60 is then pushed forwardly (i.e., downwardly as viewed in FIG. 1) to force air through the opening 64 in the forward end wall 50 of the pressure regulator housing 38. As illustrated by arrows in FIG. 4, the air forced through the opening 64 travels in two paths. Some of the air passes through the radial slots 76, 76 . . . 76 in the forwardly facing surface of the valve housing 70, beneath the central portion 90 of the valve disc 68, and through the opening 80 in the central portion of the valve housing 70 and into the piston chamber 95. As air is forced into the piston chamber 95 it forces the piston member 96 rearwardly in the piston chamber 95, against the force of spring 98.

Some of the air forced through the opening 64 travels through the spiral groove 92 on the upper surface of the valve disc 68, between the rearwardly facing surface of the forward end wall 50 of the housing and the forwardly facing surface of the valve disc, through the central opening 62 in the forward end wall 50, through the central fitting 34, through the connecting tube 30, through the lumen 24 on the endotracheal tube 14, out of the lumen opening 26 and into the inflatable cuff 22 to inflate the cuff 22 against the wall of the trachea 20, as shown in FIG. 2.

The spring 98 in the pressure regulator housing 38 will force the piston member 96 forwardly in the piston chamber 95 to equalize the pressure in the piston chamber 95 and in the inflated cuff 22. Since the pressure regulator housing 38 is transparent, the position of the piston 96 in the housing 38 serves as a visual indication of the amount of pressure in the cuff 22. It is contemplated that some sort of indicia (e.g., color coding) will be provided on the pressure regulator housing 38 to assist attending personnel in determining the proper pressure to which the cuff 22 should be inflated.

After the cuff 22 has been inflated to the desired pressure, the syringe 58 is removed from the syringe fitting 52 and the outer or proximal end of the endotracheal tube 14 may be connected to a suitable breathing apparatus (e.g., a respirator, not shown) to introduce air under pressure through the endotracheal tube 14 and into the patient's lungs. Typically, such a respirator may intermittently introduce air into the patient's lungs at a frequency of between about six and fifteen cycles per minute, at pressures which range from about zero centimeters of water to about 15 centimeters of water. By way of example, the spring 98 which urges the piston member 96 forwardly in the pressure regulator housing 38 may be selected so as to maintain an optimum pressure in the inflated cuff 22 of about 12 or 12.5 centimeters of water.

It will thus be appreciated that when the air being introduced from the respirator to the patient's lungs is at peak pressure (e.g., about 15 centimeters of water), the pressure of the air so introduced would tend to collapse the cuff 22 away from the wall 20 of the trachea and thereby permit air to escape through the annular space between the outer surface of the endotracheal tube 14 and the tracheal wall 20.

The improved pressure regulator 10 of the present invention prevents such collapse of the cuff 22. When the pressure of the air being introduced into the patient's lungs exceeds about 12 or 12.5 centimeters of water, the increased pressure acts against the inflated cuff 22 to rapidly force air from the cuff 22, through the lumen 24, through the connecting tube 30, through the central opening 62 in the forward end wall 50 of the pressure regulator housing 38 and against the central portion 90 of the valve disc 68. This relatively rapid surge of pressure will force the central portion 90 of the valve disc 68 against the annular valve seat 82 in the central portion of the valve housing 70 to seal off the opening 80 therein and prevent air from passing into the piston chamber 95. Accordingly, the quantity of air necessary to prevent collapse of the cuff 22 will be retained in the cuff during the period of high respiration pressure, thereby preventing the escape of respiration gas upwardly through the patient's trachea.

The improved pressure regulator 10 of the present invention also functions to permit relatively slow increases in air pressure in the inflated cuff 22 to be transferred into the pressure regulator housing 38. Such slow increases in the pressure of the air in the inflated cuff 22 may occur by virtue of the air being introduced through the endotracheal tube 14 migrating through the pores of the material of the cuff 22, and it is desirable to relieve such increased pressure in the cuff.

When the pressure of the air in the inflated cuff 22 exceeds the optimum pressure (e.g., about 12 or 12.5 centimeters of water), this slow increase of pressure will be transferred through the lumen 24, through the connecting tube 30, through the central fitting 34 on the forward end wall 50 of the pressure regulator housing 38, through the central opening 62 and into the valve chamber between the rearwardly facing surface of the forward end wall 50 of the housing 38 and the forwardly facing surface of the valve disc 68. The air forced slowly into the valve chamber may then travel through the spiral groove 92 in the forwardly facing surface of the valve disc 68, around the outer periphery of the valve disc 68, through the radial grooves 76 in the forwardly facing surface of the valve housing 70, beneath the central portion 90 of the valve disc 68, through the central opening 80 in the valve housing 70 and into the piston chamber 95 to force the piston further rearwardly against the force of the spring 98.

It will thus be appreciated that the improved pressure regulator of the present invention functions to (1) prevent relatively rapid pressure increases imposed by a respirator or breathing apparatus to which the endotracheal tube is connected from collapsing the inflatable cuff to prevent the escape of air between the cuff and the wall of the trachea, and (2) permits relatively slow pressure increases in the inflatable cuff to be transferred into the regulator, thereby preventing over-inflation of the cuff.

It will also be appreciated that the improved pressure regulator of the present invention provides attending personnel with a visual indication of the air pressure in the cuff by simply viewing the position of the piston member 96 and the overlying rolling diaphragm 102 in the transparent housing 38.

It is contemplated that various modifications and additions may be made to the preferred embodiment of the present invention described above without departing from the spirit and scope of the invention. Accordingly, it is intended that the scope of this patent be limited only by the scope of the appended claims.

I claim:

1. An improved pressure regulator for regulating the fluid pressure in an inflatable cuff on an endotracheal tube or the like comprising:

a pressure regulator housing;
   means defining first and second openings in said pressure regulator housing; said first opening being adapted to be connected to an inflatable cuff, and said second opening being adapted to be connected to a source of fluid under pressure for inflating an inflatable cuff connected to said first opening;
   a valve housing disposed in said pressure regulator housing; said valve housing defining a valve chamber in fluid communication with said first and second openings;
   a valve member disposed in said valve chamber;
   a piston chamber in said pressure regulator housing exterior of said valve chamber;
   a piston member in said piston chamber; and
   means defining a fluid flow passage between said valve chamber and said piston chamber;
   said valve member being responsive to relatively rapid increases in fluid pressure in said first opening in said housing to block said fluid flow passage between said valve chamber and said piston chamber.

2. An improved pressure regulator according to claim 1, wherein said pressure regulator housing includes a forward end wall, a rear end wall, and a peripheral wall extending between said forward and rear end walls; and wherein said means defining said first and second openings in said pressure regulator housing comprises means defining first and second openings in said forward end wall.

3. An improved pressure regulator according to claim 2, and further including a flexible diaphragm having an outer periphery sealingly secured to the peripheral wall of said housing.

4. An improved pressure regulator according to claim 1, wherein said means defining a fluid flow passage between said valve chamber and said piston chamber comprises an opening in said valve housing; said valve member being responsive to relatively rapid increases in fluid pressure at said first opening to cover said opening in said valve housing and block the flow of fluid to said piston chamber.

5. An improved pressure regulator according to claim 4, wherein said valve member comprises a flexible member.

6. An improved pressure regulator according to claim 5, wherein said valve housing includes a valve seat thereon, and wherein said opening in said valve housing is in said valve seat; said valve seat including a seating surface having means defining a fluid passage therein for permitting fluid to flow around said flexible valve member, through said opening in said valve seat and into said piston chamber in response to relatively slow increases in fluid pressure at said first opening in said pressure regulator housing.

7. An improved pressure regulator according to claim 1, and further comprising means defining a fluid passage between said first and second openings in said pressure regulator housing.

8. An improved pressure regulator according to claim 7, wherein said means defining a fluid passage between said first and second openings includes means defining fluid flow restricting means in said fluid passage.

9. An improved pressure regulator according to claim 1, and further comprising means defining a fluid flow restricting passage in said valve member between said first and second openings.

10. An improved pressure regulator according to claim 9, wherein said valve member comprises a flexible disc member, and wherein said fluid flow restricting passage comprises means defining a generally spiral groove in said flexible disc member.

11. An improved pressure regulator according to claim 1, wherein said pressure regulator housing is constructed of a relatively transparent material, whereby when said first opening in said housing is connected to an inflatable member the position of said piston in said housing serves as a visual indication of the fluid pressure in such inflatable member.

12. An improved pressure regulator according to claim 1, and further comprising spring means normally biasing said piston member toward said valve housing.

13. An improved pressure regulator according to claim 1, wherein said pressure regulator housing includes a peripheral wall; and further incuding a flexible diaphragm having an outer periphery sealingly secured to said peripheral wall of said housing; said flexible diaphragm overlying said piston member and being disposed between said piston member and said valve housing.

14. An improved pressure regulator for regulating the pressure in an inflatable cuff on an endotracheal tube or the like, comprising:
  a pressure regulator housing having a forward end wall, a rear end wall and a peripheral wall extending between said forward and rear end walls;
  means defining a first opening in said forward end wall of said pressure regulator housing which is adapted to be connected to an inflatable cuff; and
  means defining a second opening in said forward end wall of said pressure regulator housing which is adapted to be connected to a source of air for introducing air into said pressure regulator housing and into an inflatable cuff to which said first opening is adapted to be connected;
  a valve assembly disposed in said pressure regulator housing adjacent said first and second openings in said forward end wall of said housing;
  said pressure regulator housing defining a piston chamber between said rear end wall and said valve assembly;
  said valve assembly including a valve housing having a support surface and an upstanding peripheral wall on said support surface, said upstanding peripheral wall having an upper end secured to said forward end wall of said pressure regulator housing so as to define a valve chamber between said forward end wall of said pressure regulator housing and said support surface of said valve housing; said first and second openings in said forward end wall of said pressure regulator housing opening into said valve chamber;
  means defining an opening extending through said support surface of said valve housing to establish fluid communication between said valve chamber and said piston chamber;
  a flexible valve disc disposed in said valve chamber;
  said flexible valve disc being adapted to flex in response to rapid pressure surges introduced through said first opening in said forward end wall of said pressure regulator housing to close said opening in said support surface of said valve housing to prevent such rapid pressure surges from being introduced into said piston chamber;
  said flexible valve disc including an upper surface facing said forward end wall of said pressure regulator housing and a lower surface resting on said support surface of said valve housing;
  means defining a flow restricting spiral groove on said upper surface of said flexible valve disc;
  means defining a plurality of air flow passages in said support surface of said valve housing;
  whereby, relatively slow pressure increases in an inflatable cuff to which said first opening in said forward end wall of said valve housing is adapted to be connected will cause air to flow through said first opening in said forward end wall, through said flow restricting spiral groove on said upper surface of said valve disc, through said plurality of air flow passages in said support surface of said valve housing and through said opening in said support surface of said valve housing and into said piston chamber;
  a piston member disposed in said piston chamber;
  spring means in said pressure regulator chamber biasing said piston member towards said valve assembly; and
  a flexible diaphragm member having an outer periphery secured to said peripheral wall of said pressure regulator housing; said flexible diaphragm member overlying said piston member;
  said pressure regulator housing being constructed of a relatively transparent material, whereby when said first opening in said forward end wall of said housing is connected to an inflatable cuff the position of said piston and said flexible diaphragm in said piston chamber serves as a visual indication of the air pressure in such inflatable cuff.

* * * * *